United States Patent [19]
Weiner et al.

[11] Patent Number: 5,935,577
[45] Date of Patent: Aug. 10, 1999

[54] TREATMENT OF AUTOIMMUNE DISEASE USING TOLERIZATION IN COMBINATION WITH METHOTREXATE

[75] Inventors: Howard L. Weiner, Brookline; Ahmad Al-Sabbagh, West Roxbury, both of Mass.; Patricia A. Nelson, Palo Alto, Calif.

[73] Assignee: Autoimmune Inc., Lexington, Mass.

[21] Appl. No.: 09/012,806

[22] Filed: Jan. 23, 1998

Related U.S. Application Data

[60] Provisional application No. 60/036,722, Jan. 24, 1997.

[51] Int. Cl.[6] .......................... A61K 39/00; A61K 38/17; A61K 38/28; A61K 38/00
[52] U.S. Cl. ........................ 424/184.1; 424/810; 514/2; 514/3; 514/4; 514/21; 514/826; 514/866; 514/885; 514/903; 514/253
[58] Field of Search ................................ 424/184.1, 810; 514/2, 3, 4, 21, 826, 866, 885, 903, 253

[56] References Cited

U.S. PATENT DOCUMENTS

| | | | |
|---|---|---|---|
| 5,399,347 | 3/1995 | Trentham et al. | 424/184.1 |
| 5,571,499 | 11/1996 | Hafler et al. . | |
| 5,571,500 | 11/1996 | Hafler et al. . | |
| 5,641,474 | 6/1997 | Hafler et al. | 424/43 |
| 5,645,820 | 7/1997 | Hafler et al. | 424/41 |
| 5,720,955 | 2/1998 | Weiner et al. | 424/184.1 |
| 5,783,188 | 7/1998 | Weiner et al. | 424/184.1 |
| 5,843,445 | 12/1998 | Weiner et al. | 424/184.1 |
| 5,856,446 | 1/1999 | Weiner et al. | 530/356 |

OTHER PUBLICATIONS

Trentham, D.E. et al. Science 261:1727–1730, Sep. 1993.
Barnett, M.L. et al. Arthritis & Rheumatism 39(4):623–628, Apr. 1996.

*Primary Examiner*—David Saunders
*Assistant Examiner*—F. Pierre VanderVegt
*Attorney, Agent, or Firm*—Darby & Darby

[57] ABSTRACT

A combination of a mucosally administrable bystander antigen and an orally, enterally, or parenterally administrable methotrexate is employed to make a pharmaceutical formulation and to treat or prevent autoimmune disease. The amounts of bystander antigen and methotrexate are effective in combination to suppress autoimmune response associated with the autoimmune disease

23 Claims, 8 Drawing Sheets

Cumulative Paulus 20 Response

TREATMENT OF AUTOIMMUNE DISEASE USING TOLERIZATION IN COMBINATION WITH METHOTREXATE

This application claims priority pursuant to 35 U.S.C. § 119 from Provisional Patent Application Serial No. 60/036,722 filed Jan. 24, 1997, the disclosure of which is hereby incorporated in its entirety.

FIELD OF THE INVENTION

This invention pertains to the field of treatment of autoimmune diseases by tolerization. This invention also relates to the field of treatment of autoimmune diseases by administration of methotrexate.

BACKGROUND OF THE INVENTION

Autoimmune diseases are characterized by an abnormal immune response directed against normal autologous (self) tissues.

Based on the type of immune response (or immune reaction) involved, autoimmune diseases in mammals can generally be classified in one of two different categories: cell-mediated (i.e., T-cell-mediated) or antibody-mediated (i.e., β-cell mediated) disorders. Non-limiting examples of T-cell-mediated autoimmune diseases include multiple sclerosis (MS), rheumatoid arthritis (RA), the autoimmune stage of diabetes mellitus (juvenile-onset or Type 1 diabetes) and autoimmune uveoretinitis (AUR). Antibody-mediated autoimmune diseases include without limitation myasthenia gravis (MG), autoimmune thyroiditis (AT), and systemic lupus erythematosus (SLE).

Both categories of autoimmune diseases are currently being treated with drugs that suppress immune responses systemically in a non-specific manner, i.e., drugs incapable of selectively suppressing the abnormal immune response. One such drug is methotrexate, a biological response modifier that selectively inhibits fast growing cells. However, methotrexate has significant toxic and other side effects and eventually induces "global" immunosuppression in the subject being treated. In other words, prolonged treatment with a normal course of methotrexate downregulates the normal protective immune response against pathogens, thereby increasing the risk of infection. In addition, patients subjected to prolonged global immunosuppression have an increased risk of developing severe medical complications from the treatment, such as malignancies, liver, and kidney failure.

To treat autoimmune disease, methotrexate is normally administered once a week in a high dose of, e.g., 7.5 to 25 mg. Such treatment is commonly used to treat rheumatoid arthritis, and has been effectively used to treat multiple sclerosis (Goodkin et al., Ann. Neurology. 37:30, 1995). Although oral administration is most common, methotrexate is also commercially available for parenteral administration for such treatment.

Recently, new methods and pharmaceutical formulations have been found that are useful for treating autoimmune diseases (and related T-cell mediated inflammatory disorders such as allograft rejection and retroviral-associated neurological disease). These treatments induce tolerance, orally or mucosally, e.g. by inhalation, using as tolerizers autoantigens, bystander antigens, or disease-suppressive fragments or analogs of autoantigens or bystander antigens. Such treatments are described in PCT Patent Applications Nos. PCT/US93/01705 filed Feb. 25, 1993, PCT/US91/01466 filed Mar. 4, 1991, PCT/US90/07455 filed Dec. 17, 1990, PCT/US90/03989 filed Jul. 16, 1990, PCT/US91/07475 filed Oct. 10, 1991, PCT/US93/07786 filed Aug. 17, 1993, PCT/US93/09113 filed Sep. 24, 1993, PCT/US91/08143 filed Oct. 31, 1991, PCT/US91/02218 filed Mar. 29, 1991, PCT/US93/03708 filed Apr. 20, 1993, PCT/US93/03369 filed Apr. 9, 1993, and PCT/US91/07542 filed Oct. 15, 1991. Autoantigens and bystander antigens are defined below.

Intravenous administration of autoantigens (and fragments thereof containing immunodominant epitopic regions of their molecules) has been found to induce immune suppression through a mechanism called clonal anergy. Clonal anergy causes deactivation of only immune attack T-cells specific to a particular antigen, the result being a significant reduction in the immune response to this antigen. Thus, the autoimmune response-promoting T-cells specific to an autoantigen, once anergized, no longer proliferate in response to that antigen. This reduction in proliferation also reduces the immune reactions responsible for autoimmune disease symptoms (such as neural tissue damage that is observed in MS). There is also evidence that oral administration of autoantigens (or immunodominant fragments) in a single dose and in substantially larger amounts than those that trigger "active suppression" may also induce tolerance through anergy (or clonal deletion).

A method of treatment has also been disclosed that proceeds by active suppression. Active suppression functions via a different mechanism from that of clonal anergy. This method, discussed extensively in PCT Application PCT/US93/01705, involves oral or mucosal administration of antigens specific to the tissue under autoimmune attack. These are called "bystander antigens" and are defined below. This treatment causes regulatory (suppressor) T-cells to be induced in the gut-associated lymphoid tissue (GALT), or bronchial associated lymphoid tissue (BALT), or most generally, mucosa associated lymphoid tissue (MALT) (MALT includes GALT and BALT). These regulatory cells are released in the blood or lymphatic tissue and then migrate to the organ or tissue afflicted by the autoimmune disease and suppress autoimmune attack of the afflicted organ or tissue. The T-cells elicited by the bystander antigen (which recognize at least one antigenic determinant of the bystander antigen used to elicit them) are targeted to the locus of autoimmune attack where they mediate the local release of certain immunomodulatory factors and cytokines, such as transforming growth factor beta (TGF-β), interleukin-4 (IL-4), and/or interleukin-10 (IL-10). Of these, TGF-β is an antigen-nonspecific immunosuppressive factor in that it suppresses immune attack regardless of the antigen that triggers the attack. (However, because oral or mucosal tolerization with a bystander antigen only causes the release of TGF-β in the vicinity of autoimmune attack, no systemic immunosuppression ensues.) IL-4 and IL-10 are also antigen-nonspecific immunoregulatory cytokines. IL-4 in particular enhances Th2 response, i.e., acts on T-cell precursors and causes them to differentiate preferentially into Th2 cells at the expense of Th1 responses. IL-4 also indirectly inhibits Th1 exacerbation. IL-10 is a direct inhibitor of Th1 responses. After orally tolerizing mammals afflicted with autoimmune disease conditions with bystander antigens, increased levels of TGF-β, IL-4 and IL-10 are observed at the locus of autoimmune attack. Chen, Y. et al., Science, 265:1237–1240, 1994. The bystander suppression mechanism has been confirmed by von Herreth et al., J. Clin. Invest., 96:1324–1331, September 1996.

It has also been disclosed that oral or parenteral administration of Type I interferon, or polypeptides having Type I interferon activity, either alone or in conjunction with oral or mucosal administration of autoantigens or bystander antigens, is beneficial in reducing the symptoms of autoimmune disease. Suboptimal doses of Type I ($\alpha$ or $\beta$) interferon potentiate the tolerizing effect of the autoantigens and bystander antigen. This work has been described in more detail in PCT application no. PCT/US95/04120, filed Apr. 07, 1995. Type I interferon, especially $\beta$-IFN, is known to have certain immunomodulatory properties, e.g., inhibition of the activity of $\gamma$-interferon (IFN-$\gamma$). IFN-$\gamma$ has been shown to exacerbate MS, and may be involved in the pathogenesis of MS lesions. Thus, IFN-$\beta$ appears to have a beneficial effect due in part to its ability to inhibit IFN-$\gamma$ expression by T-cells.

PCT/US95/04512, filed Apr. 07, 1995, describes use of Th2-enhancing cytokines in conjunction with oral tolerization employing autoantigens or bystanders antigens.

None of these applications, however, describes any form of tolerization in combination with methotrexate therapy. Also, prior to the present invention, it was not known whether methotrexate, which inhibits cell division, would inhibit cells involved in mediating mucosal tolerance in the treatment of autoimmune disease.

One object of the invention is to allow administration of less toxic amounts of methotrexate in the treatment of autoimmune diseases.

An additional object is to allow administration of methotrexate in more frequent administrations in order to reduce the amount that is administered at one time.

Another object is to provide a treatment for autoimmune disease that is more effective than either administration of methotrexate alone or administration of an oral, or more generally, a mucosal tolerizing agent alone.

SUMMARY OF THE INVENTION

In one embodiment, the present invention relates to a method for treating autoimmune disease. The method involves mucosally administering a bystander antigen. The method also involves orally, enterally, or parenterally administering methotrexate. The amounts of bystander antigen and methotrexate are effective in combination to suppress autoimmune response associated with the autoimmune disease.

In another embodiment, the present invention relates to a pharmaceutical combination for oral or enteral administration to treat autoimmune disease. The combination comprises methotrexate and a bystander antigen, the amounts of the bystander antigen and methotrexate being effective in combination to suppress autoimmune response associated with the autoimmune disease.

In another embodiment, the present invention relates to a method for treating autoimmune disease. The method involves mucosally administering an autoantigen. The method also involves orally, enterally, or parenterally administering methotrexate. The amounts of autoantigen and methotrexate are effective in combination to suppress autoimmune response associated with the disease.

In another embodiment, the present invention relates to a pharmaceutical combination for oral or enteral administration to treat autoimmune disease. The combination comprises methotrexate and an autoantigen, the amounts of the autoantigen and methotrexate being effective in combination to suppress autoimmune response associated with the autoimmune disease.

DETAILED DESCRIPTION OF THE INVENTION

Figure 1:
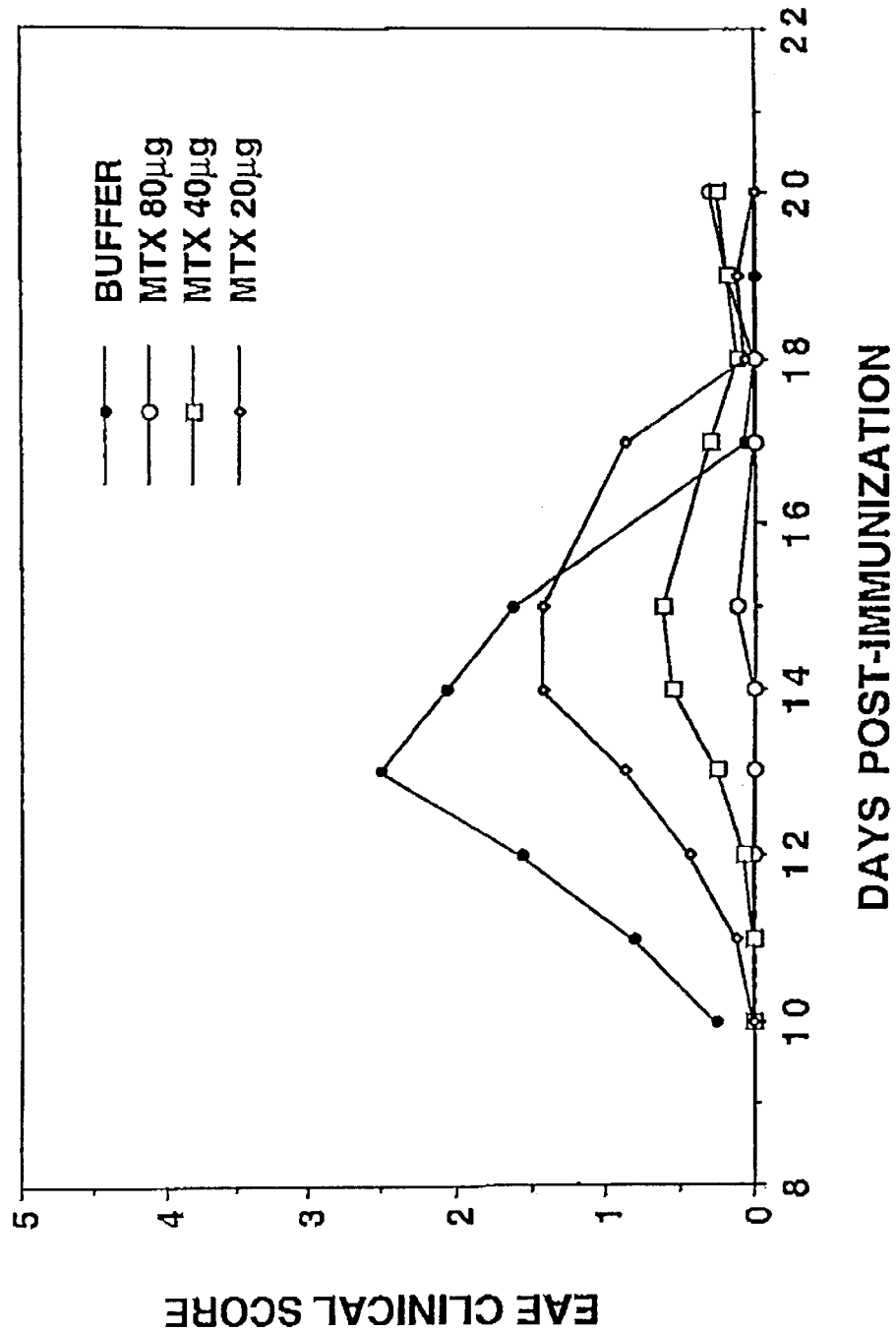
FIG. 1 is a graph that shows the effects on EAE clinical scores of administering optimal and sub-optimal dosages of methotrexate.

It has been discovered that oral or, more generally mucosal, administration of a bystander antigen (or an autoantigen), in conjunction with oral or parenteral administration of methotrexate results in suppression of autoimmune reaction that is substantially augmented compared to the effect of each treatment separately.

In one embodiment, the present invention allows a lower amount of methotrexate to be administered for treatment of autoimmune disease than would otherwise be necessary (a suboptimal dose). This is highly advantageous because of methotrexate's high toxicity. Thus, for example, the suppressive effect of administering a combination of methotrexate and MBP has been found to be more effective than the effect of administering either alone.

Methotrexate has been found not to prevent treatment by mucosal tolerization, even though methotrexate is known to inhibit cell division, i.e., it has not detrimentally affected the cells mediating treatment of autoimmune disease by tolerance. Furthermore, administration of tolerizing agent has been found not to interfere with methotrexate's inhibitory effects.

Furthermore, the "rebound" effect that is associated with methotrexate administration can be reduced. Administration of methotrexate, in EAE rats and in humans, results in a rebound of disease following suppression (after the course of administrations is completed). Such a rebound is not observed with oral, or mucosal, tolerization. The combination of MBP and methotrexate does not result in a rebound effect. Thus, administering methotrexate does not interfere with this benefit of mucosal tolerization.

In addition, it has been determined that the combination of methotrexate and tolerizing agent can be frequently administered at lower doses per administration. While methotrexate is normally administered once a week in a high dose to treat autoimmune disease, the combination of the invention has been found to be effective when administered three times a week at lower doses. As described above, administering an overall lower dose of methotrexate according to the invention acts to reduce toxicity. Administering that lower dose in subdivided form at intervals during the week further acts to reduce toxicity.

Thus, for example, if methotrexate is normally administered by itself at an optimal dose of 10 mg per week to treat an autoimmune disease, it is possible, according to the method of the invention to administer methotrexate at a dosage of about 3 mg, three times a week, in conjunction with an effective amount of tolerizing agent. Alternately, it is possible to administer methotrexate once a week at a suboptimal dose of, e.g. 5 mg, in conjunction with an effective amount of tolerizing agent. Alternately, a suboptimal dose of 2 mg, three times a week, can be administered with an effective amount of tolerizing agent.

While the invention can be viewed as an improvement on the treatment of autoimmune conditions with methotrexate, it can also be viewed as an improvement on the treatment of autoimmune diseases by oral (or mucosal) tolerization.

Definitions

The following terms, when used in this disclosure, have the meanings ascribed to them below:

"Bystander antigen" or "bystander" is a protein, protein fragment, peptide, glycoprotein, or any other immunogenic substance (i.e. a substance capable of eliciting an immune response) that (i) is, or is derived from, a component specific to the organ or tissue under autoimmune attack; and (ii) upon oral or enteral administration elicits regulatory (suppressor) T-cells (which can be of the CD4+ or CD8+ type) that cause at least one antigen-nonspecific immunosuppressive factor or immunoregulatory cytokine (such as TGF-$\beta$, IL-4 or IL-10) to be released at the organ or tissue under attack and thereby suppress immune attack cells that contribute to autoimmune destruction. The term includes but is not limited to autoantigens and fragments thereof involved in autoimmune attack. In addition, the term includes antigens normally not exposed to the immune system which become exposed in the locus of autoimmune attack as a result of autoimmune tissue destruction. An example is heatshock proteins, which although not specific to a particular tissue are normally shielded from contact with the immune system.

"Bystander suppression" is suppression at the locus of autoimmune attack of cells that contribute to autoimmune destruction; this suppression is mediated by the release of one or more immunosuppressive factors (including Th2-enhancing cytokines and Th1-inhibiting cytokines) from suppressor T-cells elicited by the ingestion (or inhalation) of a bystander antigen and recruited to the site where cells contributing to autoimmune destruction are found. The result is antigen-nonspecific but locally restricted downregulation of the autoimmune responses responsible for tissue destruction.

"Autoimmune disease" is defined herein as a spontaneous or induced malfunction of the immune system of mammals, including humans, in which the immune system fails to distinguish between foreign immunogenic substances within the mammal and/or autologous substances and, as a result, treats autologous tissues and substances as if they were foreign and mounts an immune response against them. The term includes human autoimmune diseases and animal models therefor.

"Autoantigen" is any substance or a portion thereof normally found within a mammal that, in an autoimmune disease, becomes the primary (or a primary) target of attack by the immune system. The term also includes antigenic substances that induce conditions having the characteristics of an autoimmune disease when administered to mammals. Additionally, the term includes peptic subclasses consisting essentially of immunodominant epitopes or immunodominant epitope regions of autoantigens. Immunodominant epitopes or regions in induced autoimmune conditions are fragments of an autoantigen that can be used instead of the entire autoantigen to induce the disease. In humans afflicted with an autoimmune disease, immunodominant epitopes or regions are fragments of antigens specific to the tissue or organ under autoimmune attack and recognized by a substantial percentage (e.g. a majority though not necessarily an absolute majority) of autoimmune attack T-cells.

"Treatment" is intended to include both prophylactic treatment to prevent or delay the onset of an autoimmune disease (or to prevent the manifestation of clinical or subclinical, e.g., histological, symptoms thereof), as well as therapeutic suppression or alleviation of symptoms after the manifestation of autoimmune disease, by abating autoimmune attack and preventing or slowing down autoimmune tissue destruction. "Abatement", "suppression" or "reduction" of autoimmune attack or reaction encompasses partial reduction or amelioration of one or more symptoms of the attack or reaction. A "substantially" increased suppressive effect (or abatement or reduction) of autoimmune reaction means a significant decrease in one or more markers or histological or clinical indicators of autoimmune reaction or disease. Nonlimiting examples are a reduction by at least 1 unit in limb paralysis score or in arthritis score, a significant reduction in the frequency of autoreactive T-cells, and a reduction of at least about 0.5 units in insulitis scoring (measured, e.g., as described in Zhang et al., *PNAS,* 1991, 88:10252–10256).

"Oral" administration includes oral, enteral or intragastric administration. By-inhalation administration also accomplishes a tolerizing effect in autoimmune disease.

"Parenteral" administration includes subcutaneous, intradermal, intramuscular, intravenous, intraperitoneal or intrathecal administration.

Administration "in conjunction with" encompasses simultaneous and sequential administration, as well as administration in combined form or separately.

Animal Models

Throughout the present specification, reference is made to various model systems that have been developed for studying autoimmune diseases. Experimental autoimmune encephalomyelitis (EAE) has been studied in mice and other rodent species as a model for Multiple Sclerosis (MS). Those of ordinary skill in the art recognize that many of the potential immune therapies for MS are first tested in this animal model system. The disease is induced by immunization with myelin basic protein (MBP), myelin oligodendrocyte protein (MOG), or proteolipid protein (PLP) and an adjuvant (such as Complete Freund's Adjuvant, "CFA"). The antigen that is used to induce the disease is the autoantigen in the model. This treatment, with either antigen, induces either a monophasic or an exacerbating/remitting form of demyelinating disease (depending on the type and species of rodent and well-known details of induction). The induced disease has many of the characteristics of the autoimmune disease MS and serves as an animal model therefor. Furthermore, the successful treatment of EAE by oral tolerization, and the parallel success in decreasing the frequency of disease-inducing cells in humans, and, in many cases, ameliorating the symptoms of MS, using oral administration of myelin, validates the use of EAE as a model system for predicting the success of different oral tolerization regimens.

Immunization with *Mycobacterium tuberculosis* or with CFA in oil into the dorsal root tail of susceptible mammals induces a disease used as a model for human rheumatoid arthritis. In like manner, immunization with Type II collagen with an adjuvant will also induce a disease (collagen-induced arthritis or "CIA") that serves as a model for human rheumatoid arthritis. These animal models also serve as good predictors of successful oral tolerization using bystander antigens.

Immunization of Lewis rats with S-antigen or IRBP-antigen (InterPhotoReceptor Binding Protein) and an adjuvant induces autoimmune uveoretinitis. Finally, a model for Type I diabetes develops spontaneously in the NOD Mouse.

One or more of the above disclosed model systems may be employed to demonstrate the efficacy and improved treatment provided by the present invention. In fact, the animal models are particularly suitable for testing therapies involving bystander suppression, precisely because this suppression mechanism is antigen-nonspecific. In the case of oral tolerization, therefore, the suppression of symptoms obtained in the model is independent of many of the actual or potential differences between a human autoimmune disorder and an animal model therefor.

The above animal models can be thus used to demonstrate the successful use of the present invention. For example, a multiple sclerosis autoantigen, bovine myelin, orally administered to humans in a double-blind study conferred a considerable benefit to a significant patient subset (Weiner, H. et al. *Science* 259:1321–1324, 1993). In addition, rheumatoid arthritis symptoms, such as joint tenderness, AM stiffness, grip strength, etc., were successfully suppressed in humans receiving oral collagen (0.1–0.5 mg single dose daily). (Trentham, D. et al., *Science* 261:1727, 1993.) Finally, preliminary human trials with oral S-antigen showed encouraging results for uveoretinitis. Large scale human studies are presently being conducted for multiple sclerosis, uveoretinitis, rheumatoid arthritis and diabetes. The predictive value of animal models for oral tolerization treatment of autoimmune diseases is supported by these human clinical studies.

Description of Bystander Suppression

In contrast to clonal anergy, suppression mediated by mucosal administration of bystander antigens is brought about by elicitation of targetable immunoregulatory T-cells that release one or more immunosuppressive factors, such as transforming growth factor-beta (TGF-β); and/or Th2-enhancing cytokines, such as interleukin 4 (IL-4); and/or interleukin 10 (IL-10) at the locus of the autoimmune attack. These regulatory T-cells do not release high levels of IL-2 or γ-IFN. Because regulatory T-cells are elicited, the mechanism at work is referred to as active suppression. The immunoregulatory cytokines released by the elicited regulatory cells are antigen-nonspecific, even though these regulatory T-cells release (or induce the release of) immunoregulatory cytokines only when triggered by an antigenic determinant identical to one on the mucosally administered antigen. Recruitment of the immunoregulatory T-cells to a locus within a mammal where cells contributing to the autoimmune destruction of an organ or tissue are concentrated allows for the release of immunoregulatory substances in the vicinity of the autoimmune attack and suppresses all types of immune system cells responsible for such attack.

Because the T-suppressor cells have been elicited in response to mucosal tolerization with a tissue- or organ-specific antigen, the target for the suppressor T-cells is the organ or tissue under immune attack in the particular autoimmune disease where the destructive cells are concentrated. Thus, the bystander antigen may be an autoantigen or a peptide containing an immunodominant epitope of an autoantigen. Alternatively, the bystander may be another tissue-specific antigen that is not an autoantigen; hence, the autoantigen (or autoantigens) involved in the particular disease being treated need not be identified.

In more detail, an example of the active suppression mechanism of bystander suppression for a tissue-specific (bystander) antigen is as follows: After a tissue-specific (bystander) antigen is administered orally (or enterally, i.e., directly into the stomach) it passes into the small intestine, where it comes into contact with the Peyer's patches and villi, which are collections of a large number of immunocytes located under the intestinal wall. These cells, in turn, are in communication with the immune system, including the spleen and lymph nodes. The result is that suppressor (CD8+ or CD4+) T-cells are induced, released into the blood or lymphatic circulation, and then recruited to the area of autoimmune attack, where they cause the release of TGF-β and/or other immunoregulatory substances that downregulate the activated helper T-cells as well as the B-cells directed against the mammal's own tissues. Chen, Y. et al., *Science*, 1994 supra. Suppression induced in this manner is antigen-nonspecific. However, the resulting tolerance is specific for the particular autoimmune disease, i.e., for a particular tissue under autoimmune attack, by virtue of the fact that the bystander antigen is specific for the tissue under attack and suppressor cells elicited by ingestion of the bystander antigen suppress the immune attack cells that are found at or near the tissue being damaged.

Bystander antigens and autoantigens (as well as fragments and analogs of any of them) can be purified from natural sources (the tissue or organ where they normally occur) and can also be obtained using recombinant DNA technology, in bacterial, yeast, insect (e.g. baculovirus) and mammalian cells using techniques well-known to those of ordinary skill in the art. Amino acid sequences for many potential and actual bystander antigens are known: See, e.g., Hunt, C. et al *PNAS (USA)*, 82:6455–6459, 1985 (heat shock protein hsp70); Burkhardt, H., et al., *Eur. J. Immunol.* 21:49–54, 1991 (antigenic collagen II epitope); Tuohy, V. K., et al., *J. Immunol.* 142:1523–1527, 1989 (encephalitogenic determinant of mouse PLP in mice); Shinohara, T. et al., In *Progress in Retinal Research,* Osborne, N. & Chader, J. Eds, Pergamon Press 1989, pp. 51–55 (S-antigen); Donoso, L. A., et al., *J. Immunol.* 143:79–83, 1989 (IRBP); Borst, D. E., et al., *J. Biol. Chem.* 264:115–1123, 1989 (IRBP); Yamaki, K. et al., *FEBS* 234:39–43, 1988 (S-antigen); Donoso, L. A. et al., *Eye Res.* 7:1087, 1988 (IRBP); Wyborski, R. J., et al., *Mol. Brain Res.* 8:193–198, 1990 (GAD).

The amino acid sequences for bovine and mouse PLP; bovine, human, chimpanzee, rat, mouse, pig, rabbit, guinea pig MBP; human and bovine collagen alpha-1(II) and bovine collagen alpha-l(I); chicken collagen II, and human insulin are well-known and published and these antigens can be synthesized by recombinant techniques, as is well-known in the art. Fragments of these antigens can be chemically synthesized or also synthesized by recombinant techniques.

Some tissue-specific antigens are commercially available: e.g., insulin, glucagon, myelin basic protein, myelin, collagen I, collagen II, proteolipid protein, etc.

Bystander antigens can be routinely identified. Any antigen from the afflicted tissue is a potential bystander. The potential bystander can be fed to mammals, and spleen cells or circulating T-cells from, e.g., the blood or cerebrospinal fluid in the case of EAE or MS, from these mammals can be removed and stimulated in vitro with the same antigen. T-cells elicited by stimulation can be purified and supernatants can be tested for their content of TGF-β, IL-4, IL-10, or other immunoregulatory substances. In particular, TGF-β can be measured quantitatively and/or qualitatively by ELISA using preferably a suitable commercially available polyclonal or most preferably monoclonal antibody raised against TGF-β (e.g. R&D Systems, Minneapolis, Minn.; Celtrix Pharmaceuticals, Santa Clara, Calif.). Miller, A. et al., *J. Immunol.*, 148:1106, 1992. Alternatively, another known assay for TGF-β detection can be employed, such as that described in the Examples below, using a commercially available mink lung epithelial cell line. If the bystander antigen elicits T-suppressor cells that do not release TGF-β, the T-cells can be similarly tested for secretion of IL-4 or IL-10 (antibodies for IL-4 and IL-10 are commercially available, e.g., from Pharmingen, San Diego, Calif.). Tissue-specific antigens that are not effective bystanders are those so segregated from the inflammatory locus (of autoimmune attack) so that the immunoregulatory cytokines released are too far removed from the locus of inflammation to exert a suppressive effect.

The efficacy of mucosally induced bystander suppression can be assessed, e.g., by: diminution in certain inflammation markers, such as the number of activated T-cell clones directed against the organ or tissue that is the target of autoimmune attack; decrease in IL-2 or IFN-γ levels at the same locus; histological evaluation of the afflicted organ or tissue (e.g. by biopsy or magnetic resonance imaging); or reduction in the number and/or severity of clinical symptoms associated with an autoimmune disease.

Use of Tolerizing Antigens—Dosages

The tolerance induced by the bystander antigens of this invention is dose-dependent over a broad range of oral (or enteral) or inhalable dosages. However, there are minimum and maximum effective dosages. In other words, active suppression of the clinical and histological symptoms of an autoimmune disease occurs within a specific dosage range, which, however, varies from disease to disease, mammal to mammal, and bystander antigen to bystander antigen. For example, when the disease is PLP-induced EAE in mice, the suppressive dosage range when MBP is used as the bystander is from about 0.1 to about 1 mg/mouse/feeding (with feedings occurring about every other day e.g., 5–7 feedings over a 10–14-day period). A most preferred dosage is 0.25 mg/mouse/feeding. For suppression of the MBP induced disease in rats, the MBP suppressive dosage range is from about 0.5 to about 2 mg/rat/feeding and the most preferred dosage is 1 mg/rat/feeding. An effective dosage range for humans with MS, when MBP is used as the oral tolerizer, is between about 1 and about 100, preferably between about 1 and about 20 mg MBP per day (administered every day or on alternate days for a period of time ranging from several months to several years) with the optimum being between about 7 and 10 mg per day.

For rheumatoid arthritis, effective dosage range for humans receiving either Type I or II or Type III collagen is between about 0.005 and about 1 mg per day. A preferred dosage is between about 0.005 and about 0.5 mg per day.

Monitoring of the patient may be desirable in order to optimize the dosage and frequency of administration. The exact amount and frequency of administration to a patient may vary depending on the stage, frequency of manifestation and severity of the patient's disease and the physical condition of the patient, as is well-appreciated in the art. Such optimization is preferably effected on a case-by-case basis. Optimization of the dosage necessary for immune suppression involves no more than routine experimentation, given the guidelines disclosed herein.

Assessment of the disease severity can be accomplished according to well-known methods depending on the type of disease. Such methods include without limitation:

MS: severity and number of attacks over a period of time; progressive accumulation of disability (which can be measured, e.g., on the Expanded Disability Status Scale); number and extent of lesions in the brain (as revealed, e.g., by magnetic resonance imaging); and frequency of autoreactive T-cells.

EAE: limb paralysis which can be scored as follows: 0—no disease; 1—decreased activity, limp tail; 2—mild paralysis, unsteady gait; 3—moderate paraparesis, limbs splayed apart; 4—tetraplegia; and 5—death.

RA: joint swelling, joint tenderness, morning stiffness, grip strength, joint imaging techniques.

AUR: visual acuity; number of T-cells in the eye and "cloudiness" in the eye.

Type I Diabetes: pancreatic beta cell function (assessed, e.g., by OGTT glucose tolerance test).

NOD Model: insulitis and delay of diabetes onset.

CIA: Arthritis score based on number of affected joints in each of four paws and grading each on an arbitrary scale of 1–4 as follows: 0=normal; 1=redness only; 2=redness plus swelling; 3=severe swelling; and 4=joint deformity. The total arthritis score is the sum of the scores for all paws. Maximum arthritis score is the highest score for an animal over the course of the disease. According to this grading method the highest arthritis score possible is 16 (4 paws×4 score-per-paw).

Stabilization of symptoms, under conditions wherein control patients or animals experience a worsening of symptoms, is one indicator of efficacy of a suppressive treatment. Another measure of improvement is the ability to reduce or discontinue other medications, e.g., steroids or other anti-inflammatory medications, and biologic response modifiers. The optimum dosage of a bystander antigen or autoantigen is one generating the maximum beneficial effect assessed as described above. An effective dosage causes at least a statistically or clinically significant attenuation of at least one marker, symptom or histological evidence characteristic of the disease being treated as described above. (Clinically significant-attenuation is one observed by a clinician of ordinary skill in the field of a particular autoimmune disease.)

When combined with methotrexate treatment, the dosage of bystander antigen (or autoantigen) may equal that which would have been used if the bystander antigen (or autoantigen) was administered alone, except that the combination is more effective in abating autoimmune reaction.

Where the dosage of methotrexate is as high as that where methotrexate is used alone, the combination with a bystander antigen or autoantigen can result in enhanced suppressive effects. Alternately, a sub-optimal dosage of methotrexate can be administered in order to lessen methotrexate's toxic effects. In this case, the enhanced suppression achieved by the combination, can, for example, be as high as that achieved by an optimal dose of methotrexate alone.

Ascertaining the effective dosage range as well as the optimum amount of bystander antigen is determined using conventional methods and the teachings of the present application. For example, dosages for mammals and human dosages can be determined by beginning with a relatively low dose (e.g. 1 microgram), progressively increasing it (e.g. logarithmically) and measuring the number of TGF-beta (and/or IL-4 or IL-10) secreting cells and/or assessing the number and activation of immune attack T-cells in the blood (e.g. by limiting dilution analysis and ability to proliferate) and/or assessing the disease severity, as described above. The optimum dosage generates the maximum amount of suppressive cytokines in the blood and/or causing the greatest decrease in disease symptoms. An effective dosage causes at least a statistically or clinically significant attenuation of at least one symptom characteristic of the disease being treated.

The maximum effective dosage of a bystander antigen can be ascertained by testing progressively higher dosages in animals and then extrapolating to humans. For example, based on the dosages given above, for rodents, the maximum effective dose of MBP for humans has been estimated between 50 and 100 mg/feeding. Similarly, the maximum effective amount of Collagen Type II for humans has been estimated at about 1 mg/day.

The present invention can also be advantageously used to prevent the onset of an autoimmune disease in susceptible individuals at risk for an autoimmune disease. For example, methods for the identification of patients who are at risk for developing Type 1 diabetes are extant and reliable and have been recently endorsed by the American Diabetes Association (ADA). Various assay systems have been developed which (especially in combination) have a high predictive value assessing susceptibility to Type 1 diabetes (*Diabetes Care* 13: 762–775, 1990). Details of one preferred screening test are available to those of ordinary skill in the art (Bonifacio, E. et al., *The Lancet* 335: 147–149, 1990).

From a practical point of view, preventing the onset of autoimmune disease is of most importance in type I diabetes. Other autoimmune diseases (e.g., MS, RA, AT and AUR) are declared at an earlier stage of tissue destruction, before substantial tissue damage has taken place; therefore preventive treatment of these diseases is not as important as in type I diabetes. In type I diabetes, it is best to intervene with an effective treatment prior to the substantial destruction of substantially all of the pancreatic islet cells. After the islet cells are destroyed, the treatment may not be effective unless used in conjunction with an inlet cell transplant.

A non-limiting list of autoimmune diseases and tissue- or organ-specific confirmed or potential bystander antigens and autoantigens effective in the treatment of these diseases when administered in an oral or inhalable form are set forth in Table 1 below. Combinations of antigens listed for each individual disease can also be administered.

Bystander antigens and autoantigens can also be administered by inhalation. The bystander amounts that need to be inhaled are generally smaller than those for oral administration. Effective amounts for inhalation therapy can be assessed using the same methodologies provided above.

| Autoimmune Disease | Affected Tissue | Bystander Antigen | Source | Type |
|---|---|---|---|---|
| Type 1 Diabetes | pancreatic beta cells | glucagon; insulin; glutamic acid decarboxylase (GAD); heatshock protein | | |
| Multiple Sclerosis | myelinated neurons | MBP; PLP; DM20; myelin associated glycoprotein (MAG); myelin oligodendrocyte glycoprotein (MOG); heatshock protein | J. Chromatog. Biomed. Appl. 526:535 (90) | purification |
| Rheumatoid Arthritis | connective tissue | collagen I, II or III; RO/SS-A; RO/SS-B-LA; heatshock protein | J. Immunol. Meth 121:21 9 (89) 151:177 (92) | purification purification |
| Autoimmune Uveitis | eye | S-antigen; IRBP | Exp. Eye Res. 56:463 (93) | cDNA |
| Myasthenia Gravis | muscle | acetylcholine receptor; heatshock protein | Eur. J. Pharm. 172:231 (89) | purification |
| Male Infertility | sperm | NASP (post-acrosomal sperm protein) | Biol. Reprod. 43:559 (90) | cDNA |
| Myositis | muscle | Jo-1 antigen; heatshock protein | Biol. Chem. H-S. 368:531 (87) | purification |
| Pemphigus | skin | desmoglein | Eur. J. Cell Biol. 55:200 (91) | cDNA |
| Autoimmune Thyroiditis | thyroid | thyroglobulin | | |

For any autoimmune disease, extracts of the relevant tissue, as well as specific bystander antigens or fragments thereof, can be used as mucosal tolerizers. In other words, the bystander antigen need not be purified. For example, myelin (which could be derived from different species) has been used for MS, pancreatic cell extracts have been used for Type 1 diabetes, splenic cell extracts have been used to prevent allograft rejection (this is not an autoimmune phenomenon), and muscle extracts have been used to treat myositis. However, administration of one or more individual antigens or fragments is preferred.

Thus, according to the present invention, when treating Type 1 diabetes, an effective amount (determined as described above) of glucagon can be administered orally. Glucagon is specifically present in the pancreas. Glucagon, however, is clearly not an autoantigen because it is not expressed in pancreatic beta cells which are destroyed in the course of Type 1 diabetes (glucagon is found exclusively in alpha cells, a different cell type). Thus, glucagon is a "pure" bystander: it does not appear to have any autoantigen activity. (Presumably, the bystander activity of glucagon results from its high local concentration in the pancreatic intercellular milieu due to its secretion from alpha cells.)

Insulin has bystander activity for Type 1 diabetes. It is not at present known whether insulin is also an autoantigen, although anti-insulin autoantibodies are found in Type 1 patients. However, whatever the mechanism of action, oral, enteral or inhalable insulin preparations are effective in suppressing Type 1 diabetes and animal models therefor by preventing autoimmune destruction of pancreatic beta cells.

For multiple sclerosis and animal models therefor, both disease inducing and noninducing fragments of MBP have bystander activity not only for MBP-induced disease but also for PLP-induced disease. In rats, feeding of bystander antigen generates mostly $CD8^+$ suppressor cells which are class I restricted, whereas in mice both $CD8^+$ suppressors and $CD4^+$ regulatory cells are generated (the latter thought to probably be Class II restricted). Chen, Y. et al. *Science,* 1994, supra.

For rheumatoid arthritis and animal models therefor, Type-I, Type-II and Type-III collagen have activity as mucosal tolerizers. Other collagens are likely to be similarly active.

For uveoretinitis and its animal model, S-antigen and IRBP and fragments thereof have bystander activity.

Fragments of bystander antigens can also be employed. Useful fragments can be identified using the overlapping peptide method and T-cells from fed animals can be tested for secretion of TGF-β, and/or IL-4 and/or IL-10, and can further be identified by subtype ($CD8^+$ and/or $CD4^+$).

Mucosally administered bystander antigens elicit regulatory T-cells and thereby induce the production and/or release of TGF-β and/or IL-4 and IL-10. One such T-cell has been identified in mice orally tolerized against EAE as a CD4+ suppressor T-cell, and a CD8+ suppressor T-cell has been identified in rats. Even immunodominant epitopes of autoantigens, e.g. MBP, are capable of inducing such regulatory T-cells. Additional such epitopes can be identified by feeding a bystander antigen to a mammal and isolating from the mammal T-cells that recognize a fragment of the antigen (and thus identifying suppressive fragments), or by identifying T-cells from a bystander fed mammal that can adoptively transfer protection to naive (not-fed) animals.

Autoantigen administration is carried out as disclosed in PCT Applications PCT/US93/01705 filed Feb. 25, 1993, PCT/US91/01466 filed Mar. 4, 1991, PCT/US90/07455 filed Dec. 17, 1990, PCT/US90/03989 filed Jul. 16, 1990, PCT/US91/07475 filed Oct. 10, 1991, PCT/US93/07786 filed Aug. 17, 1993, PCT/US93/09113 filed Sep. 24, 1993, PCT/US91/08143 filed Oct. 31, 1991, PCT/US91/02218 filed Mar. 29, 1991, PCT/US93/03708 filed Apr. 20, 1993, PCT/US93/03369 filed Apr. 9, 1993, and PCT/US91/07542 filed Oct. 15, 1991 mentioned above.

In addition, other cytokine and non-cytokine synergists can be conjoined in the treatment to enhance the effectiveness of oral tolerization with methotrexate. Oral and parenteral use of other cytokine synergists (Type I interferons) has been described in PCT/US95/04120, filed Apr. 07, 1995. Administration of Th2 enhancing cytokines is described in PCT application no. PCT/US95/04512, filed Apr. 07, 1995. For example, IL-4 and IL-10 can be administered in the manner described in PCT/US95/04512. Non-limiting examples of non-cytokine synergists for use in the present invention include bacterial lipopolysaccharides from a wide variety of gram negative bacteria such as various subtypes of *E. coli* and Salmonella (LPS, Sigma Chemical Co., St. Louis, Mo.; Difco, Detroit, Mich.; BIOMOL Res. Labs., Plymouth, Pa.), Lipid A (Sigma Chemical Co., St. Louis, Mo.; ICN Biochemicals, Cleveland, Ohio; Polysciences, Inc., Warrington, Pa.); immunoregulatory lipoproteins, such as peptides covalently linked to tripalmitoyl-S-glycarylcysteinyl-seryl-serine ($P_3$ C55) which can be obtained as disclosed in Deres, K. et al. (*Nature,* 342:561–564, 1989) or "Braun's" lipoprotein from *E. coli* which can be obtained as disclosed in Braun, V., *Biochim. Biophys. Acta* 435:335–337, 1976; and cholera toxin β-chain (CTB) the synergist ability of which has been described (though not in connection with abatement of autoimmune reaction) by Sun, J-B et al., 1994 PNAS (USA) 91, November 1994. Lipid A is preferred over LPS for use in the present invention because it is less toxic than the entire LPS molecule. LPS for use in the present invention can be extracted from gram-negative bacteria and purified using the method of Galanes et al. (*Eur. J. Biochem.* 9:245, 1969) and Skelly, R. R., et al. (*Infect. Immun.* 23:287, 1979). The effective dosage range for noncytokine synergists for mammals is from about 15 µg to about 15 mg per kg weight and preferably 300 µg–12 mg per kg weight. The effective dosage range for oral Type I interferon for mammals is from 1,000–150,000 units with no maximum effective dosage having been discerned.

Ascertaining the optimum regimen for administering both the tolerizing agent and methotrexate is determined in light of the information disclosed herein and well known information concerning administration of bystander antigens, autoantigens, and methotrexate. Routine variation of dosages, combinations, and duration of treatment is performed under circumstances wherein the severity of autoimmune reaction can be measured. Useful dosage and administration parameters are those that result in reduction in autoimmune reaction, including a decrease in number of autoreactive T-cells, or in the occurrence or severity of at least one clinical or histological symptom of the disease.

The tolerizing agent is preferably administered within 24 hours of administration of methotrexate. More preferably, it is administered at the same time as methotrexate. Most preferably, both are administered in a combined oral formulation.

Methotrexate for use in the invention is commonly commercially available in both oral and parenteral dosage forms. Alternately, methotrexate is conventionally formed in an oral or parenteral dosage form, using carriers and other agents as further described below.

Each oral (or enteral) formulation according to the present invention may comprise inert constituents including pharmaceutically acceptable carriers, diluents, filers, solubilizing or emulsifying agents, and salts, as is well-known in the art. For example, tablets may be formulated in accordance with conventional procedures employing solid carriers well-known in the art. Capsules employed in the present invention may be made from any pharmaceutically acceptable material, such as gelatin, or cellulose derivatives. Sustained release oral delivery systems and/or enteric coatings for orally administered dosage forms are also contemplated, such as those described in U.S. Pat. No. 4,704,295, issued Nov. 3, 1987; U.S. Pat. No. 4,556,552, issued Dec. 3, 1985; U.S. Pat. No. 4,309,404, issued Jan. 5, 1982; and U.S. Pat. No. 4,309,406, issued Jan. 5, 1982.

Examples of solid carriers include starch, sugar, bentonite, silica, and other commonly used carriers. Further non-limiting examples of carriers and diluents which may be used in the formulations of the present invention include saline, syrup, dextrose, and water.

Examples of formulations for tolerizing agents that are administered by inhalation are provided in PCT/US90/07455, filed Dec. 17, 1990. The pharmaceutical formulations for administration by inhalation of the present invention may include, as optional ingredients, pharmaceutically acceptable carriers, diluents, solubilizing and emulsifying agents, and salts of the type that are well-known in the art. Examples of such substances include normal saline solutions, such as physiologically buffered saline solutions, and water.

The route of administration of tolerizing antigens according to this alternate embodiment of the present invention is in an aerosol or inhaled form. The antigens can be administered as dry powder particles or as an atomized aqueous solution suspended in a carrier gas (e.g. air or $N_2$). Preferred aerosol pharmaceutical formulations may comprise for example, a physiologically-acceptable buffered saline solution containing between about 1 mg and about 300 mg of the antigens.

Dry aerosol in the form of finely divided solid particles of tolerizing antigens that are not dissolved or suspended in a liquid are also useful in the practice of the present invention. The tolerizing antigens may be in the form of dusting powders and comprise finely divided particles having an average particle size of between about 1 and 5 microns, preferably between 2 and 3 microns. Finely divided particles may be prepared by pulverization and screen filtration using techniques well known in the art. The particles may be administered by inhaling a predetermined quantity of the finely divided material, which can be in the form of a powder.

Specific non-limiting examples of the carriers and/or diluents that are useful in the by-inhalation pharmaceutical formulations include water and physiologically-acceptable buffered saline solutions such as phosphate buffered saline solutions pH 7.0–8.0. Additional non-limiting examples of suitable carriers or diluents for use in by-inhalation pharmaceutical formulations or dosage forms of the present invention are disclosed in U.S. Pat. No. 4,659,696, issued Apr. 21, 1987, U.S. Pat. No. 4,863,720, issued Sep. 5, 1989 and U.S. Pat. No. 4,698,332, issued Oct. 6, 1987.

The pharmaceutical formulations of the present invention may be administered in the form of an aerosol spray using for example, a nebulizer such as those described in U.S. Pat. No. 4,624,251 issued Nov. 25, 1986; U.S. Pat. No. 3,703,173 issued Nov. 21, 1972; U.S. Pat. No. 3,561,444 issued Feb. 9, 1971 and U.S. Pat. No. 4,635,627 issued Jan. 13, 1971. The aerosol material is inhaled by the subject to be treated.

Other systems of aerosol delivery, such as the pressurized metered dose inhaler (MDI) and the dry powder inhaler as disclosed in Newman, S. P. in *Aerosols and the Lung*, Clarke, S. W. and Davia, D. eds. pp. 197–224, Butterworths, London, England, 1984, can be used when practicing the present invention.

Aerosol delivery systems of the type disclosed herein are available from numerous commercial sources including Fisons Corporation (Bedford, Mass.), Schering Corp. (Kenilworth, N.J.) and American Pharmoseal Co. (Valencia, Calif.).

All patent applications, patents, and literature references cited in this specification are hereby incorporated by reference in their entirety. In case of conflict, the description including the definitions and interpretations of the present disclosure prevail.

The following examples are illustrative of the present invention and are not intended to limit its scope.

EXAMPLE 1

Suppression of EAE in Rats with a Combination of an Optimal Dose of Methotrexate and a Tolerizing Agent In the experiments described below the following materials and methods were used.

Animals. Female Lewis rats were obtained from Harlan-Sprague Dawley Inc. (Indianapolis, Ind.). Animals were maintained on standard laboratory chow and water ad libitum. Animals were maintained in accordance with the guidelines for the Committee on Care of Laboratory Animals of the Laboratory Research Council (Pub. #DHEW:NIH, 85–23, revised 1985).

Antigens and Reagents. Guinea pig MBP was purified from brain tissue by the modified method of Deibler et al. (*Prep. Biochem.* 2:139, 1972). Protein content and purity were monitored by gel electrophoresis and amino acid analysis. Methotrexate was obtained from Roxane Lab. Inc. (Columbus, Ohio). Methotrexate tablets (2.5 mg) were mixed with buffer ($H_2O$: PBS in a 1:1 ratio) to obtain a concentration of 2.5 mg methotrexate/ml buffer.

Induction of Tolerance. For oral tolerance, rats were fed MBP dissolved in PBS (0.5×) by gastric intubation with a 18-gauge stainless steel animal feeding needle (Thomas Scientific, Swedesboro, N.J.). Animals were fed three times a week on Monday, Wednesday, and Friday ("QOD") for either 7 administrations or 14 administrations prior to immunization.

Induction of EAE. For actively induced disease, Lewis rats were immunized in the foot pads with 50 $\mu$l of emulsion each. 0.1 ml of emulsion contained 25 $\mu$g of guinea pig MBP and 200 $\mu$g of *Mycobacterium tuberculosis* in complete Freund's adjuvant (CFA).

Clinical evaluation. Animals were evaluated in a blind fashion every day for evidence of EAE. Clinical severity of EAE was scored as follows: 0, no disease; 1 limp tail; 2, hind limb paralysis; 3, hind limb paraplegia, incontinence; 4, tetraplegia; and 5 death. "MMCS" refers to the mean maximal clinical score. Duration of disease was measured by counting the total number of days from disease onset until complete recovery (or death) for each animal.

Statistical analysis. Clinical scales were analyzed with a two-tailed Wilcoxon rank sum test for score samples, chi square analysis was used in comparing the incidence of disease between groups, and comparison of means was performed by using the Student's t-test. For individual experiments, 5 animals were used per group.

The following Table shows the protocol for administration to each group of rats. "QOD×7" indicates administration three times a week for a total of 7 administrations. "QOD×14" indicates administration three times a week for a total of 14 administrations. The protocol was conducted twice (Study #1 and Study #2).

TABLE 1

| GROUP | CODE | MATERIAL FED | SCUEDULE |
|---|---|---|---|
| 5 RATS | A | BUFFER 1 ml | QOD × 7 |
| 5 RATS | B | BUFFER 1 ml | QOD × 14 |
| 5 RATS | C | METHOTREXATE 80 μg/1 mL | QOD × 7 |
| 5 RATS | D | METHOTREXATE 80 μg/1 mL | QOD × 14 |
| 5 RATS | E | GP-MBP 1 mg/1 ml | QOD × 7 |
| 5 RATS | F | GP-MBP 1 mg/1 ml | QOD × 14 |
| 5 RATS | G | GP-MBP 1 mg/0.5 ml + METHOTREXATE 80 μg/0.5 mL | QOD × 7 |
| 5 RATS | H | GP-MBP 1 mg/0.5 ml + METHOTREXATE 80 μG/0.5 mL | QOD × 14 |

In this experiment 80 μg of methotrexate was administered by itself, and in combination with 1 mg of GP-MBP (guinea pig MBP). The 80 μg of methotrexate administered at a frequency of three times a week corresponds to the optimal dosage of methotrexate administered to humans, when adjusted for weight. Specifically, the recommended dose for a 60 Kg person is 10 mg of methotrexate per week. Employing the chemotherapy National Cancer Institute conversion factor of 7 for rat dosages, this corresponds to administration to a 212.2 g rat of 238 μg methotrexate per week, or 80 μg methotrexate three times per week.

The results for the experiments involving administration of antigen 14 times are shown in the table below. These results demonstrated that MBP, when administered in combination with methotrexate, did not interfere with the action of methotrexate. They also confirmed that optimal suppression was achieved using 80 μg of methotrexate alone.

TABLE 2

| CODE | IMMUNOGEN | MEAN DAY OF ONSET | MMCS | INCIDENCE (N = 5) | % SUPPRESSION |
|---|---|---|---|---|---|
| Study #1 | | | | | |
| B | BUFFER 1 ml × 14 | 11.2 ± 0.5 | 2.7 ± 0.2 | 5/5 | 0 |
| D | MTX 80 μg × 14 | 00.0 ± 0.0 | 0.0 ± 0.0 | 0/5 | 100 |
| F | GP-MBP 1 mg × 14 | 16.0 ± 2.6 | 0.7 ± 0.4 | 3/5 | 74.1 |
| H | GP-MBP 1 mg + MTX 80 μg × 14 | 00.0 ± 0.0 | 0.0 ± 0.0 | 0/5 | 100 |
| Study #2 | | | | | |
| B | BUFFER 1 ml × 14 | 11.0 ± 0.3 | 2.6 ± 0.3 | 5/5 | 0 |
| D | MTX 80 μg × 14 | 00.0 ± 0.0 | 0.0 ± 0.0 | 0/5 | 100 |
| F | GP-MBP 1 mg × 14 | 17.3 ± 0.3 | 0.5 ± 0.2 | 4/5 | 80.0 |
| H | GP-MBP 1 mg + MTX 80 μg × 14 | 00.0 ± 0.0 | 0.0 ± 0.0 | 0/5 | 100 |

The table below shows results that were obtained for administration of antigen 7 times. These results demonstrated that the combination of methotrexate and MBP achieved greater suppression than either compound administered by itself. The suppression achieved with the combination was substantially greater than with either substance alone.

TABLE 3

| CODE | MATERIAL FED | MEAN DAY OF ONSET | MMCS | INCIDENCE (N = 5) | % SUPPRESSION |
|---|---|---|---|---|---|
| Study #1 | | | | | |
| A | BUFFER 1 ml × 7 | 12.0 ± 0.0 | 2.3 ± 0.1 | 5/5 | 0 |
| C | MTX 80 μg ∴ 7 | 13.2 ± 0.5 | 1.7 ± 0.2 | 5/5 | 26.1 |
| E | GP-MBP 1 mg × 7 | 12.4 ± 0.2 | 1.7 ± 0.2 | 5/5 | 26.1 |
| G | GP-MBP 1 mg + MTX 80 μg × 7 | 16.7 ± 1.2 | 0.6 ± 0.3 | 2/5 | 73.9 |
| Study #2 | | | | | |
| A | BUFFER 1 ml × 7 | 11.6 ± 0.0 | 2.3 ± 0.1 | 5/5 | 0 |
| C | MTX 80 μg × 7 | 14.0 ± 0.3 | 1.4 ± 0.1 | 5/5 | 39.1 |
| E | GP-MBP 1 mg × 7 | 12.8 ± 0.5 | 1.7 ± 0.3 | 5/5 | 26.1 |
| G | GP-MBP 1 mg + MTX 80 μg × 7 | 16.0 ± 1.0 | 0.4 ± 0.3 | 3/5 | 82.6 |

EXAMPLE 2

Suppression of EAE in Rats with a Combination of a Sub-Optimal Dose of Methotrexate and Tolerizing Agent The procedures described in Example 1 were followed, for the protocol shown below. Sub-optimal dosages of 40 μg and 20 μg were administered in combination with 1 mg of MBP over a period of 14 days. An optimal dosage of 80 μg was also administered.

TABLE 4

| GROUP | CODE | Ag FED | SCUEDULE |
|---|---|---|---|
| 8 RATS | A&B | BUFFER 1 ml | QOD × 14 |
| 8 RATS | C&D | METHOTREXATE 80 μg/1 mL | QOD × 14 |
| 8 RATS | E&F | GP-MBP 1 mg/1 ml | QOD × 14 |
| 8 RATS | G&H | GP-MBP 1 mg/0.5 ml + METHOTREXATE 80 μg/0.5 mL | QOD × 14 |
| 8 RATS | I&J | METHOTREXATE 40 μg/1 mL | QOD × 14 |
| 8 RATS | K&L | GP-MBP 1 mg/0.5 ml + METHOTREXATE 40 μg/0.5 mL | QOD × 14 |
| 8 RATS | M&N | METHOTREXATE 20 μg/1 mL | QOD × 14 |
| 8 RATS | O&P | GP-MBP 1 mg/0.5 ml + METHOTREXATE 20 μg/0.5 mL | QOD × 14 |

TABLE 5

CLINICAL DATA FROM THE EFFECT OF METHOTREXATE ON GP-MBP ORAL TOLERANCE STUDY IN LEWIS FEMALE RATS IMMUNIZED FOR EAE WITH GP-MBP/CFA
STUDY #1

| GROUP | Incidence | Mean Day Of Onset | MMCS | % EAE | % SUPPRESSION |
|---|---|---|---|---|---|
| BUFFER 1 ml | 8/8 | 10.9 ± 0.4 | 2.7 ± 0.3 | 100 | 0 |
| MTX 80 μg | 4/8 | 17.2 ± 1.2 | 0.4 ± 0.3 | 50 | 85 |
| GP-MBP 1 mg | 8/8 | 11.6 ± 0.6 | 1.6 ± 0.3 | 100 | 41 |
| GP-MBP 1 mg + MTX 80 μg | 0/8 | 00.0 + 0.0 | 0.0 ± 0.0 | 0 | 100 |
| MTX 40 μg | 8/8 | 16.0 ± 1.2 | 1.0 ± 1.2 | 100 | 63 |
| GP-MBP 1 mg + MTX 40 μg | 4/8 | 14.8 + 1.4 | 0.3 ± 1.4 | 50 | 89 |
| MTX 20 μg | 8/8 | 12.6 ± 0.5 | 1.9 ± 0.3 | 100 | 30 |
| GP-MBP 1 mg + MTX 20 μg | 7/7 | 14.1 + 1.1 | 0.6 ± 0.1 | 100 | 78 |

$$\% \text{ EAE} = \frac{\text{Number of EAE RATS}}{\text{Total Number Rats}} \times 100$$

$$\% \text{ TOLERANCE} = \frac{\text{MMCS (CONTROL)} - \text{MMCS (TEST)}}{\text{MMCS (CONTROL)}} \times 100$$

FIGS. 1–5 show clinical data from this experiment for 20 days after immunization with MBP in Complete Freund's Adjuvant.

FIG. 1 shows the results of administration of methotrexate alone. Suppression of EAE with the optimal dose (80 μg) and suboptimal doses (40 μg and 20 μg) of methotrexate can be seen to follow a dose dependent response. The graph shows a rebound effect associated with methotrexate administration, wherein, following the highest degree of suppression, at day 18, the clinical symptoms of the disease reappear.

Figure 2:
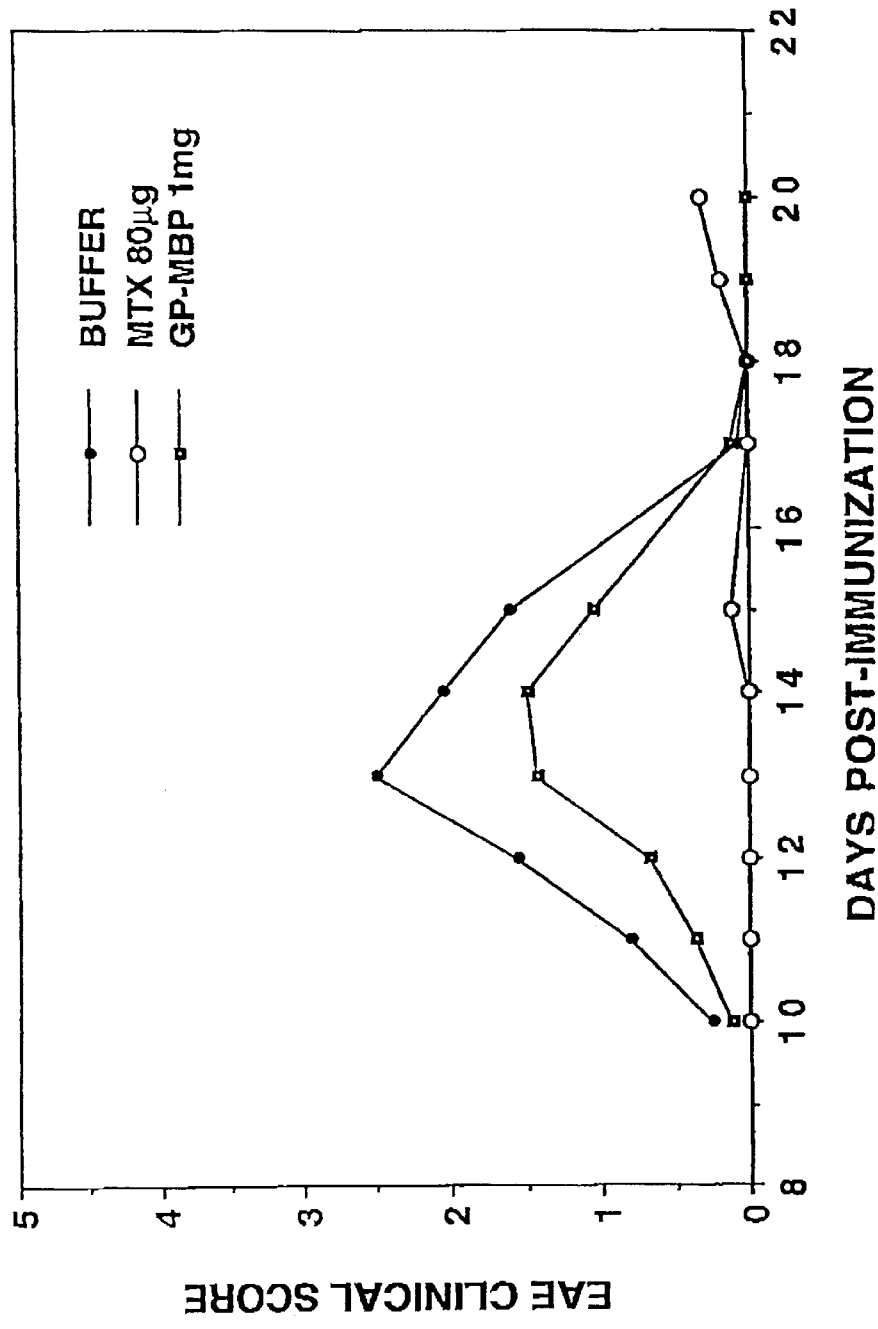
FIG. 2 is a graph that shows the effects on EAE clinical scores of administering either an optimal dose of methotrexate or a 1 mg dose of MBP.

FIG. 2 shows the effects on clinical scores of administering an optimal dose of methotrexate compared with an optimal dose of MBP. A rebound effect is seen at day 20 for rats administered methotrexate, but not for rats administered MBP.

Figure 3:
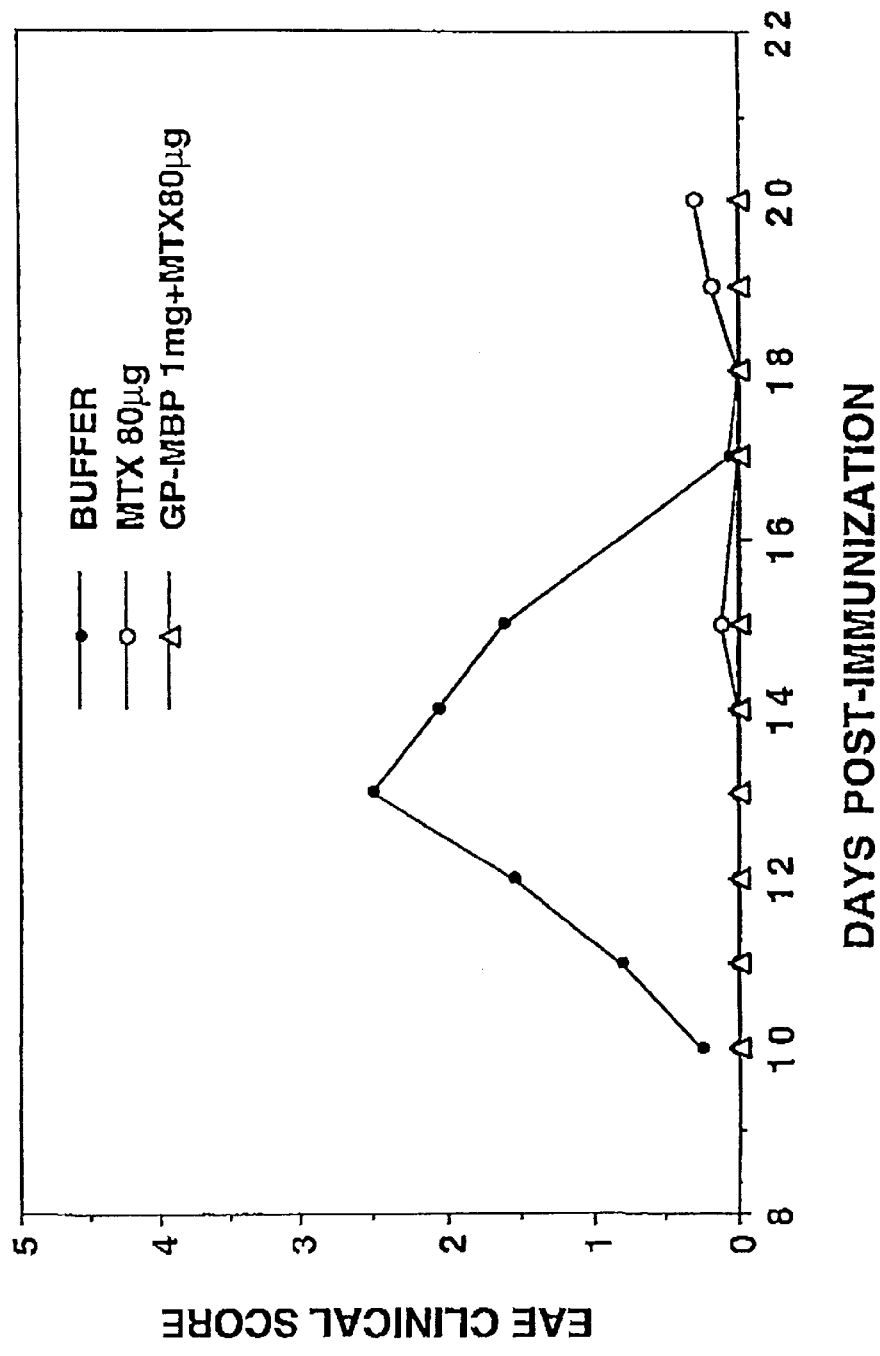
FIG. 3 is a graph that shows the effects on EAE clinical scores of combining an optimal dose of methotrexate with MBP as compared to administering an optimal dose of methotrexate alone.

FIG. 3 shows the effects on clinical scores of administering an optimal dose of methotrexate as compared with a combination of an optimal dose of methotrexate and an optimal dose of MBP. Adding MBP to the optimal dose methotrexate does not interfere with methotrexate's effects. Nor does methotrexate interfere with MBP's effect in eliminating the rebound at day 20. Thus, the effect obtained administering the combination of MBP and even an optimal dose of methotrexate is superior to that seen from administering either agent by itself.

Figure 4:
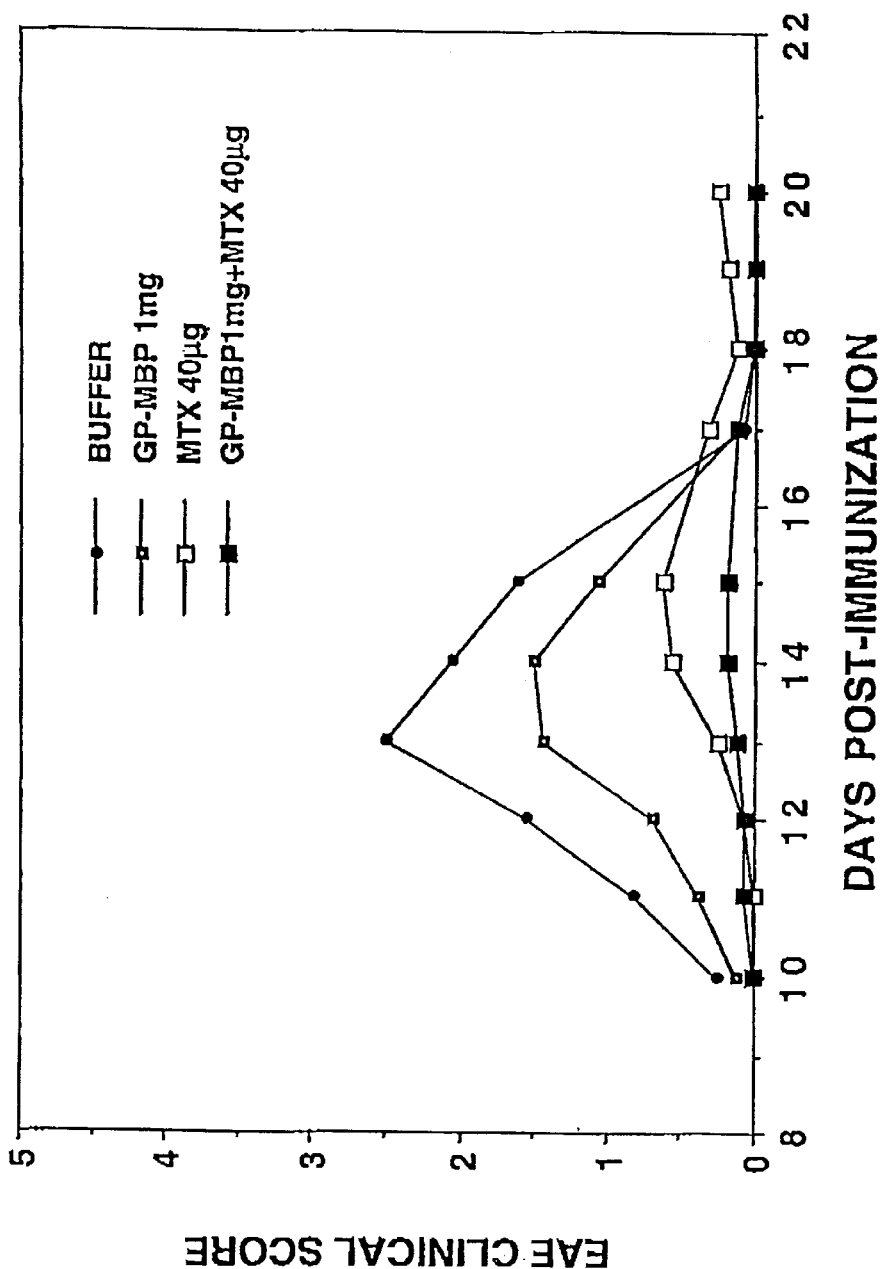
FIG. 4 is a graph showing the effects on EAE of administering a combination of a sub-optimal dose of 40 $\mu$g methotrexate and a 1 mg dose of MBP as compared with administering either alone.

FIG. 4 shows the results of administering MBP alone and a sub-optimal dose of 40 μg of methotrexate alone as compared with administering a combination of the two. The combination achieves greater suppression than that achieved with either alone, and avoids the rebound effect seen with methotrexate alone. The degree of suppression is essentially the same as that observed with the an optimal dose of methotrexate alone.

Figure 5:
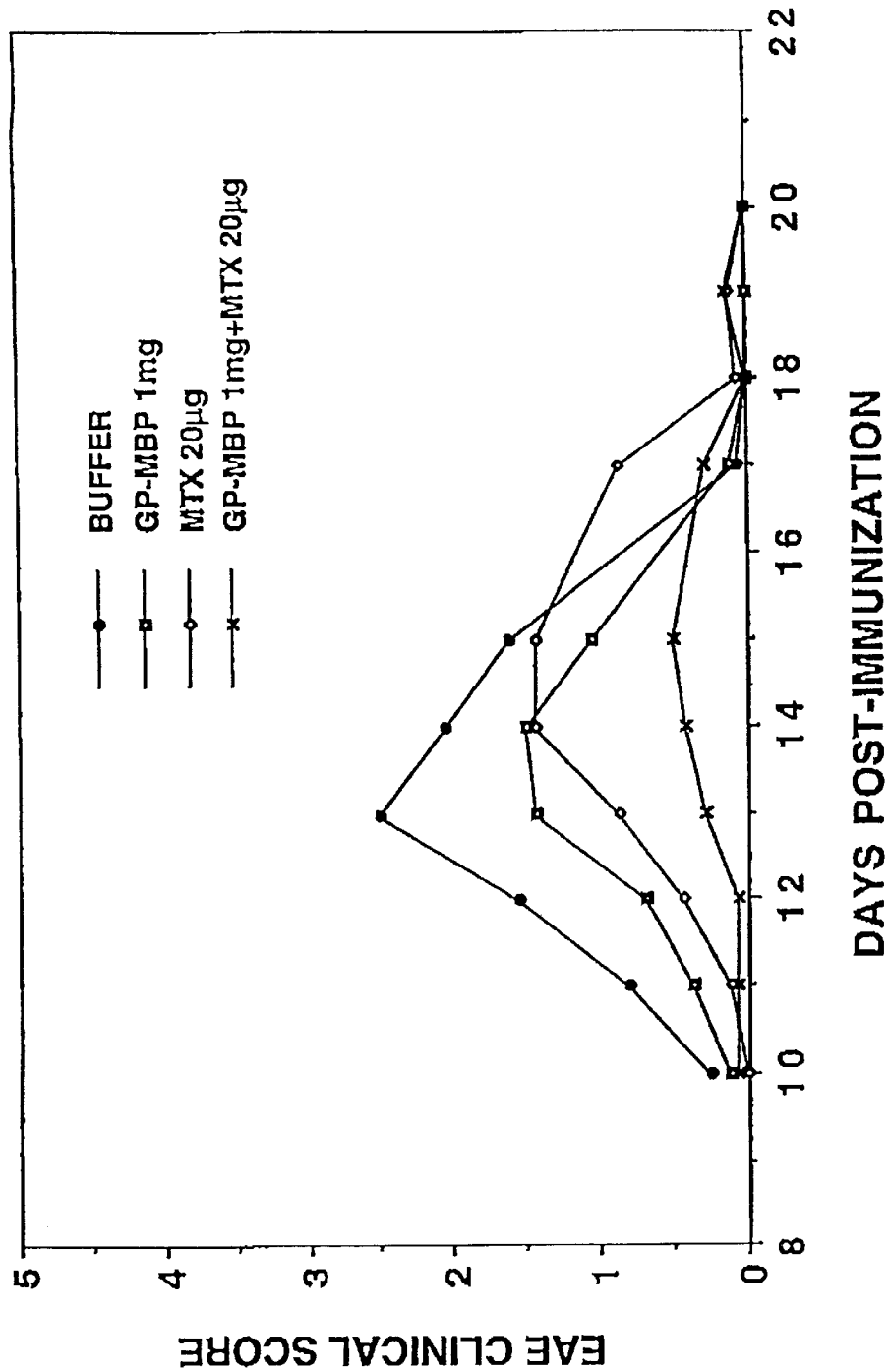
FIG. 5 is a graph showing the effects on EAE of administering a combination of a sub-optimal dose of 20 $\mu$g methotrexate and a 1 mg dose of MBP as compared with administering either alone.

FIG. 5 shows the results of administering MBP alone and a sub-optimal dose of 20 μg of methotrexate alone as compared with administering a combination of the two. The combination achieves greater suppression than that achieved with either alone. The degree of suppression is similar to that observed with an optimal dose of methotrexate alone.

Thus, according to the present invention, a lower dose of methotrexate can be administered than is optimal, but, as a result of the combination with MBP, a suppressive effect is achieved that is similar to that of an optimal dose of methotrexate alone. In addition, the combination eliminates the rebound effect associated with methotrexate administration alone.

EXAMPLE 3

Suppression of Collagen Induced Arthritis in Mice with a Combination of Methotrexate and Tolerizing Agent DBA/J1 mice were orally dosed once a day for 5 consecutive days with type II collagen (300 μg in 0.25 ml), methotrexate (10 μg in 0.25 ml), a combination of the two, or with a control solution of 0.1 N acetic acid (0.25 ml). The type II collagen was chicken sterna type II collagen (1.2 mg/ml) (Sigma Chemical Co., St. Louis, Mo.). The methotrexate was obtained as 2.5 mg tablets (Roxane Lab. Inc.). The tablets were mixed with 0.1 normal acetic acid to form a 2.5 mg/ml solution. The amount of methotrexate administered was determined based on an optimal dosage to a 60 Kg human of 10 mg/week, using the converting factor of 12 for mice (Chemotherapy National Cancer Institute), and based on an average weight of 26 g per mouse.

Three days after the final oral dose, each animal was injected intradermally into its shaved back with 0.1 ml of an emulsion containing 100 μg of type II collagen and 100 μg of *Mycobacterium butyricum*. Three weeks later, all mice were boosted with an intraperitoneal injection of 100 μg of type II collagen in 0.1 N acetic acid. Animals were monitored for onset of arthritis for 60 days. Beginning on day +10, animals are scored for signs of arthritis on a scale of 0 to 4. The arthritis score for each animal was the sum of the score for each of the four paws.

resuspended in serum-free medium for the remainder of the 72 hour culture, supernatants collected, then frozen until assayed. Determination of TGF-β content and isoform type in supernatants is performed using a mink lung epithelial cell line (American Type Culture Collection, Bethesda, MD #CCL-64) according to Danielpour et al. (Danielpour, D., et al. *J. Cell. Physiol.* 138: 79–86,1989).), and confirmed by a Sandwich Enzyme Linked Immunosorbent Assay (SELISA) assay as previously described (Danielpour et al. *Growth Factors* 2: 61–71,1989). The percent active TGF-β is determined by assay without prior acid activation of the samples.

This assay can be adapted to test any antigen which is a candidate for use as an inducer of bystander suppression. Those antigens, antigen fragments and/or amounts of antigen which produce the highest concentration of TGF-β as measured by this assay are suitable for use in the treatment method of the present invention. Alternatively, a transwell culture system, described below, can be used to indicate the

TABLE 6

Effect Of Orally Administered Methotrexate On Oral Tolerance Of Collagen Type II And Suppression Of CIA In DBA/J1 Mice Immunized With CCII/CFA

| Pretreatment | Incidence | Mean Day of Onset | MMCS | Maximum Arthritic Index | % Suppression | |
|---|---|---|---|---|---|---|
| Acetic 300 μl | 9/10 | 53.2 ± 1.1 | 6.2 ± 0.8 | 5.6 | *0.0 | **24.4 |
| Methotrexate 10 μg | 10/10 | 37.9 ± 3.6 | 8.2 ± 0.8 | 8.2 | −32.3 | 0.0 |
| CC11 300 μg (p < 0.048) | 6/10 | 41.2 ± 4.0 | 4.7 ± 1.4 | 2.8 | 24.2 | 42.7 |
| CC11 300 μg + Methotrexate 10 μg (p < 0.000) | 3/10 | 45.7 ± 6.1 | 2.8 ± 1.5 | 0.8 | 54.8 (p < 0.05) | 65.9 |

*% Suppression as compared to Acetic fed group
**% Suppression as compared to Methotrexate fed group $$\text{Maximum Arthritic Index} = \frac{\text{MMCS of arthritic mice} \times \text{Number of arthritic mice}}{\text{Total \# mice in the group}}$$

Collagen induced arthritis in DBA/1 Male mice is a far more severe clinical than rheumatoid arthritis, and although calculated based on a 10 mg dose of methotrexate in humans, 10 μg of methotrexate in mice was apparently not a high enough dose to suppress collagen induced arthritis. In fact, the severity of the disease was worse than when control buffer was administered. This may have been the result of a rebound effect, since administration of methotrexate was stopped prior to immunization.

These results showed, however, that collagen induced arthritis was suppressed to a substantially greater level when combining methotrexate with type II collagen than when administering either material alone.

EXAMPLE 4

Assay for TGF-β Induction

Measurement Of TGF-β Activity In Serum-Free Culture Supernatants

Serum free culture supernatants are collected from cells from test animals. See, for example, Kehri, et al. *J. Exp.Med.*163: 1037–1050, 1986; and Wahl, et al. *J.Immunol.* 145: 2514–2419,1990. Briefly, modulator cells are first cultured for 8 hours with the antigen (50 μl/ml) in proliferation medium. Thereafter cells are washed three times and level of TGF-β which is being produced. This culture system measures the production of TGF-β as a function of suppression of cell proliferation.

The appearance of IL-4 and/or IL-10 in culture supernatants of antigen-stimulated cells can also serve as an indicator that the antigen is suitable for use as an inducer of bystander suppression. IL-4, IL-10 (and TGF-β) can be assayed by ELISA using commercially available antibodies to each polypeptide as described in Chen, Y. et al., *Science*, 1994, supra.

Transwell Cultures. A dual chamber transwell culture system (Costar, Cambridge, Mass.), which is 24.5 mm in diameter and consists of two compartments separated by a semi-permeable polycarbonate membrane, with a pore size of 0.4 μm, is used. The two chambers are 1 mm apart, allowing cells to be co-incubated in close proximity without direct cell-to-cell contact. To measure in vitro suppression of proliferative responses in transwell cultures, $5 \times 10^4$ antigen specific line cells, raised and maintained for example, as previously described (Ben-Nun, A. et al., *Eur. J. Immunol.* 11:195, 1981), are cultured with 106 irradiated (2,500 rad) thymocytes, in 600 μl of proliferation media in the lower well. Spleen cells from orally tolerized animals (e.g. rats) or controls (fed BSA) are added to the upper well ($5 \times 10^5$ cells in 200 μl). Spleens are removed 7–14 days after the last feeding, and a single cell suspension is prepared by pressing the spleens through a stainless steel mesh. The antigen (50 µg/ml) is added in a volume of 20 µl. Because modulator cells are separated from responder cells by a semi-permeable membrane, they do not require irradiation. In some experiments, modulator cells are added in the lower well together with responder cells, and in these instances modulator cells are irradiated (1,250 rad) immediately before being placed in culture. Proliferation media consisted of RPMI 1640 (Gibco Laboratories, Grand Island, N.Y.) supplemented with $2\times10^5$ M 2-mercaptoethanol, 1% sodium pyruvate, 1% penicillin and streptomycin, 1% glutamine, 1% HEPES buffer, 1% nonessential amino acids, and 1% autologous serum. Each transwell is performed in quadruplicate. The transwells are incubated at 37° C. in a humidified 6% $CO_2$ and 94% air atmosphere for 72 hours. After 54 hours of culture, each lower well is pulsed with 4 µCi of [$^3$H]thymidine and at 72 hours split and reseeded to three wells in a round-bottomed 96-well plate (Costar) for harvesting onto fiberglass filters and counting using standard liquid scintillation techniques. Percent suppression=100× (1−Δ cpm responders cultured with modulators/Δ cpm of responders).

EXAMPLE 5

Treatment Of Rheumatoid Arthritis

Patients suffering from rheumatoid arthritis were administered either oral type II collagen alone, or a combination of oral type II collagen and oral methotrexate, as part of a clinical study designed to compare administration of oral type II collagen with administration of placebo following abrupt withdrawal from methotrexate treatment.

The patients in this study had all been previously receiving methotrexate in a maximum dose of 20 mg per week, and all suffered from severe rheumatoid arthritis typed in Functional Classes I, II, and III. Only patients classified in Functional Class IV were excluded. Functional Class IV includes patients who are limited in their ability to perform usual self-care, vocational and avocational activities. All patients exhibited at least 6 tender joints, and at least 3 swollen joints. Stable steroids, NSAIDS (non-steroidal anti-inflammatory agents, and certain analgesics, were administered to those who wished to use them).

203 patients were enrolled in the study. Immediately prior to the start of the study, methotrexate use was completely discontinued. All patients were then orally administered 20 µg/day of type II collagen in orange juice, prior to their first meal of the day.

Methods for preparation of such type II collagen are described in WO 97/25435. The type II collagen used in this study had been subjected to conventional pepsin treatment in acetic acid in order to remove telopeptides. Compositions containing 20 µg of type II collagen, methods of administration of such a dosage, and beneficial results of such administration, are described in WO 97/02837.

During the study, which lasted 24 weeks, patients were evaluated by several measures, including tender joint count and swollen joint count. Cumulative Paulus 20 response is a known measure of improvement in rheumatoid arthritis, and was used to evaluate effectiveness. Paulus et al., *Arthritis and Rheum.* 1990; 33:477–484.

At eight weeks into the study, those patients whose symptoms flared ("spiked") resumed oral treatment with commercially-available methotrexate in a dosage of between 7.5 and 10 mg/week. Of a total of 101 patients who completed the study, a comparison was made of the response between 47 patients who were administered combined type II collagen and methotrexate, and 54 patients who were administered only type II collagen.

Figure 6:
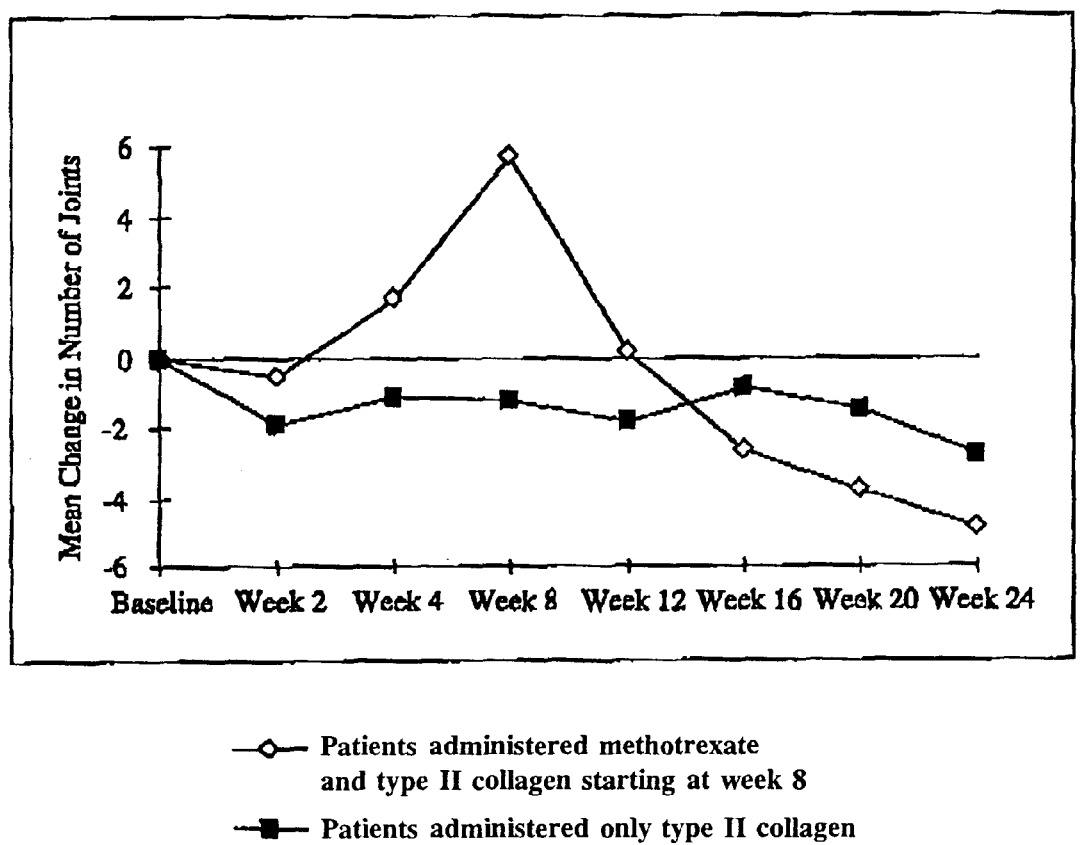
FIG. 6 is a graph showing the swollen joint count measured in rheumatoid arthritis patients who, beginning at week 8 of a clinical study, were administered either a combination of oral type II collagen and oral methotrexate (open diamonds) or only oral type II collagen (closed boxes).
Figure 7:
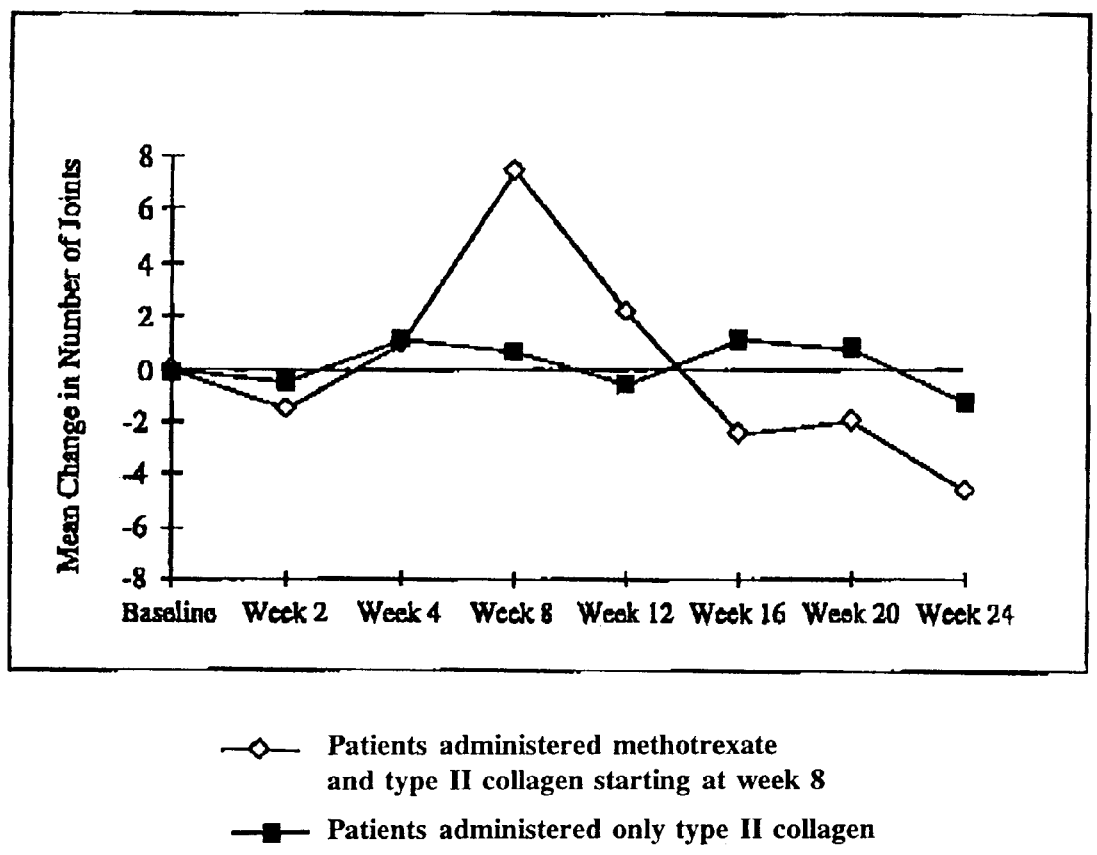
FIG. 7 is a graph showing the tender joint count measured in rheumatoid arthritis patients who, beginning at week 8 of a clinical study, were administered either a combination of oral type II collagen and oral methotrexate (open diamonds) or only oral type II collagen (closed boxes).
Figure 8:
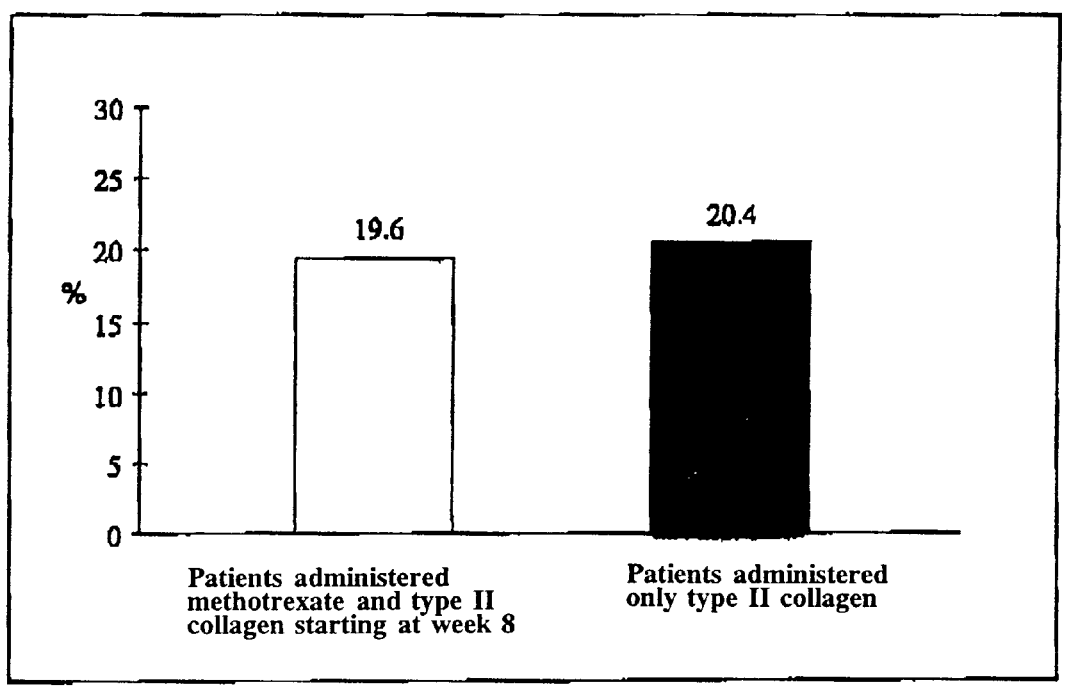
FIG. 8 shows the percent of patients achieving cumulative Paulus 20 response for those administered either a combination of type II collagen and methotrexate, or type II collagen alone.

The results of the study are shown in FIGS. 6–8. FIG. 6 shows the swollen joint count measured during the period of the study. The group of patients with exacerbated symptoms at week 8 exhibited increased swollen joint count at that time. After receiving methotrexate therapy in combination with the type II collagen therapy, this group of patients exhibited a decrease in the number of swollen joints, and after eight weeks of combination therapy (which corresponds to the 16 week mark in FIG. 6) exhibited a greater decrease in swollen joints (from their baseline number) than patients receiving only type II collagen. The results shown in FIG. 7 with respect to tender joint count followed a similar pattern.

The percent of patients achieving cumulative Paulus 20 response shown in FIG. 8 was higher for patients receiving combination therapy than for those receiving only oral type II collagen. The Paulus response for the patients receiving the colloral-methotrexate combination was calculated from the time that methotrexate was combined with type II collagen at week 8.

Thus, use of a combination of oral type II collagen and methotrexate resulted in an augmented suppression of disease as compared with use of oral type II collagen alone.

What is claimed:

1. A method for treating an autoimmune disease comprising:
   (a) mucosally administering a bystander antigen that is, or is derived from, a component specific to the organ or tissue under autoimmune attack; and
   (b) orally, enterally, or parenterally administering methotrexate;
wherein the amounts of said bystander antigen and methotrexate are effective in combination to suppress autoimmune response associated with said disease.

2. The method of claim 1 wherein said bystander antigen and said methotrexate are more effective in suppressing said response in combination compared to the suppressive effects achieved by administering each alone.

3. The method of claim 1 wherein said bystander antigen is administered orally, enterally, or by-inhalation.

4. The method of claim 1 wherein said methotrexate is administered parenterally.

5. The method of claim 1 wherein said methotrexate is administered orally.

6. The method of claim 1 wherein said disease is multiple sclerosis.

7. The method of claim 6 wherein said bystander antigen is selected from the group consisting of myelin basic protein (MBP), proteolipid protein (PLP), myelin associated glycoprotein (MAG), myelin oligodendrocyte glycoprotein (MOG) heatshock protein, and autoimmune suppressive fragments thereof.

8. The method of claim 6 wherein said bystander antigen is myelin.

9. The method of claim 1 wherein said disease is rheumatoid arthritis and said bystander antigen is selected from the group consisting of Type I collagen, Type II collagen, Type III collagen, and autoimmune suppressive fragments thereof.

10. The method of claim 1 wherein said disease is Type I diabetes therefor and said bystander antigen is selected from the group consisting of glucagon, insulin, glutamic acid decarboxylase, heat shock protein, and autoimmune suppressive fragments thereof.

11. The method of claim 1 wherein said disease is uveoretinitis and said bystander antigen is selected from the group consisting of S-antigen, interphotoreceptor retinoid binding protein (IRBP), and autoimmune suppressive fragments thereof.

12. The method of claim 1 wherein said bystander antigen and said methotrexate are administered substantially simultaneously.

13. The method of claim 1 wherein said disease is multiple sclerosis comprising orally administering a composition comprising MBP and methotrexate.

14. The method of claim 1 wherein said autoimmune disease is T-cell-mediated.

15. A method for treating multiple sclerosis comprising:
   (a) orally, enterally, or by-inhalation administering an amount of a composition comprising MBP; and
   (b) orally, enterally, or parenterally administering an amount of methotrexate;
wherein the amounts of said composition and methotrexate are effective in combination in suppressing autoimmune response associated with said disease.

16. The method of claim 15 wherein said composition comprises myelin.

17. The method of claim 15 wherein said composition and said methotrexate are administered orally.

18. The method of claim 17 wherein said composition and said methotrexate are administered substantially simultaneously.

19. The method of claim 18 wherein said composition is bovine myelin.

20. A method for treating autoimmune disease comprising:
   (a) mucosally administering an autoantigen; and
   (b) orally, enterally, or parenterally administering methotrexate;
wherein the amounts of said autoantigen and methotrexate are effective in combination to suppress autoimmune response associated with said disease.

21. The method of claim 20 wherein said disease is myasthenia gravis and said autoantigen is selected from the group consisting of acetylcholine receptor and heatshock protein.

22. A pharmaceutical formulation for oral or enteral administration to treat autoimmune disease, said formulation comprising methotrexate and a bystander antigen, wherein the amounts of said bystander antigen and methotrexate are effective in combination to suppress autoimmune response associated with said disease.

23. A pharmaceutical formulation for oral or enteral administration to treat autoimmune disease, said formulation comprising methotrexate and an autoantigen, wherein the amounts of said autoantigen and methotrexate are effective in combination to suppress autoimmune response associated with said disease.

* * * * *